(12) United States Patent
    Oh

(10) Patent No.: US 10,677,780 B2
(45) Date of Patent: Jun. 9, 2020

(54) COMPOSITIONS, KITS, AND DEVICES FOR GENERATING AND ACCURATELY MEASURING DIFFERENT OXYGEN LEVELS IN CALIBRATION AND/OR QUALITY CONTROL REAGENTS AND METHODS OF PRODUCTION AND USE THEREOF

(71) Applicant: Siemens Healthcare Diagnostics Inc., Tarrytown, NY (US)

(72) Inventor: Bong Oh, Newtonville, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 700 days.

(21) Appl. No.: 14/967,945

(22) Filed: Dec. 14, 2015

(65) Prior Publication Data

US 2016/0178571 A1    Jun. 23, 2016

Related U.S. Application Data

(60) Provisional application No. 62/093,166, filed on Dec. 17, 2014, provisional application No. 62/093,176, filed on Dec. 17, 2014.

(51) Int. Cl.
    *G01N 1/00*      (2006.01)
    *G01N 33/49*     (2006.01)
    *B01L 9/00*      (2006.01)
    *G01N 33/48*     (2006.01)

(52) U.S. Cl.
    CPC ....... *G01N 33/492* (2013.01); *G01N 33/4925* (2013.01)

(58) Field of Classification Search
    CPC .... G01N 33/492; G01N 33/49; G01N 33/487; G01N 33/483; G01N 33/48; B01L 9/54; B01L 9/00
    USPC .................................................. 422/430, 50
    See application file for complete search history.

(56) References Cited

U.S. PATENT DOCUMENTS

| 6,551,842 B1* | 4/2003 | Carpenter ............ G01N 33/558 422/68.1 |
| 2006/0182651 A1* | 8/2006 | Bailey, III .............. C02F 1/683 422/3 |
| 2007/0023296 A1* | 2/2007 | Cai .................... G01N 27/3272 205/782 |

FOREIGN PATENT DOCUMENTS

WO    2013078130 A1    5/2013

\* cited by examiner

*Primary Examiner* — Christine T Mui
(74) *Attorney, Agent, or Firm* — Dunlap Codding P.C.

(57) ABSTRACT

Compositions, kits, and devices that include calibration and/or quality control reagent(s) for monitoring the performance of blood gas, electrolyte, and/or metabolite instrumentation are disclosed. Different oxygen levels in the calibration and/or quality control reagent(s) can be generated using an oxygen scavenger. Methods of accurately measuring the oxygen levels so generated using a by-product of the oxygen scavenger are also disclosed.

8 Claims, No Drawings

COMPOSITIONS, KITS, AND DEVICES FOR GENERATING AND ACCURATELY MEASURING DIFFERENT OXYGEN LEVELS IN CALIBRATION AND/OR QUALITY CONTROL REAGENTS AND METHODS OF PRODUCTION AND USE THEREOF

CROSS REFERENCE TO RELATED APPLICATIONS/INCORPORATED BY REFERENCE STATEMENT

The subject application claims benefit under 35 USC § 119(e) of U.S. Ser. Nos. 62/093,166 and 62/093,176, both filed Dec. 17, 2014. The entire contents of the above-referenced applications are specifically incorporated herein by reference.

BACKGROUND

Liquid solutions are currently used in the calibration and quality control of sensors used in blood gas, electrolyte, and/or metabolite instrumentation. For liquid reagents with pre-determined gas concentrations, specifically oxygen, these liquid reagents are typically stored in glass ampoules or laminate barrier pouches, where the barrier material serves to maintain a pre-determined amount of dissolved gas in a solution. However, the shelf life of these solutions may still be limited as a result of degradation products and/or cross-reaction products as well as the permeability of some of the barrier materials, which leads to changes in the oxygen levels of the liquid reagents over time. Maintaining oxygen levels within reagent bags utilized with blood gas analyzers and other types of instrumentation remains a well-known problem in the art because of the oxygen permeability of most polymer-based reagent bag materials. Currently, the only means to minimize such changes in oxygen levels of liquid reagents is to use a better oxygen barrier material and/or to keep the liquid reagents under low temperature to reduce the kinetic energy of oxygen. In addition, the current systems do not have a mechanism by which to alter the level of oxygen present in reagents; thus, different bags/devices are required for each oxygen concentration level desired.

Therefore, there is a need in the art for new and improved compositions, kits, and devices for controlling and generating different oxygen levels in calibration and/or quality control reagents used to monitor the performance of, for example but without limitation, blood gas, electrolyte, and/or metabolite instrumentation, as well as methods of producing and using same, including (but not limited to) methods of accurately measuring the oxygen levels so generated in said reagents. It is to such compositions, kits, and devices for controlling and generating different oxygen levels in calibration and/or quality control reagents, as well as methods of accurately measuring the oxygen levels so generated in these reagents, that the presently disclosed and/or claimed inventive concept(s) is directed.

DETAILED DESCRIPTION

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, and/or methods disclosed and/or claimed herein can be made and executed without undue experimentation in light of the present disclosure. While the articles, compositions, and methods of the inventive concept(s) have been described in terms of particular embodiments, it will be apparent to those of skill in the art that variations may be applied to the articles, compositions and/or methods and in the steps or in the sequence of steps of the methods described herein without departing from the concept, spirit and scope of the inventive concept (s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The term "about" is used to indicate that a value includes the inherent variation of error for the device, the method being employed to determine the value and/or the variation that exists among study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "$pO_2$" as used herein will be understood to refer to the partial pressure of oxygen, that is, an amount of oxygen in a solution. "$pO_2$" may also be referred to as a level of dissolved oxygen in a solution.

The term "associate" as used herein will be understood to refer to the direct or indirect connection of two or more items.

Turning now to the presently disclosed and/or claimed inventive concept(s), a method of controlling and/or generating desired oxygen levels in-situ for on-board QC within a sensor cartridge, such as but not limited to, a single-use sensor cartridge, as well as methods of accurately measuring the oxygen levels so generated, are disclosed. In the method, a calibration and/or quality control solution containing oxygen is brought into contact with a solid reagent containing an oxygen scavenger. The oxygen scavenger reduces the amount of dissolved oxygen in the aqueous solution through a chemical reaction in which the oxygen scavenger (i.e., reducing agent) is oxidized by the oxygen; the chemical reaction is based on the reaction rate that is affected by concentration of the two reagents, the temperature at which the reaction occurs, and the reaction time. By controlling the reaction time between calibration and/or quality control solution (such as but not limited to, an air-saturated solution) and oxygen scavenger within a flow path upstream of a $pO_2$ sensor, a desired level of oxygen can be generated.

Next, an accurate concentration of the generated oxygen level in the calibration and/or quality control reagent can be calculated. In the oxygen scavenging reaction, a by-product of the reducing agent (i.e., oxygen scavenger) is produced upon oxidation thereof. For example, but not by way of limitation, when a sulfite is used as the oxygen scavenger, the by-product sulfate (i.e., the oxidation product of the sulfite) is produced. This by-product is chemically stable in aqueous solution, and its concentration is in direct proportion to the amount of oxygen consumed by the oxygen scavenger. The oxidation product of the oxygen scavenger is electrochemically active and can be electrochemically reduced, such as but not limited to, on an electrode located in a sensor array. An accurate concentration of oxygen present in the calibration and/or quality control reagent can then be calculated out from the electrochemical current generated between the electrode and the scavenging by-products.

In certain embodiments, the calibration and/or quality control solution is further defined as an air saturated oxygen solution. For purposes of illustration only, the concentration of oxygen in air-saturated deionized water (di-$H_2O$) is approximately 150 mmHG (approximately 150 μmol). Based on the methods of the presently disclosed and/or claimed inventive concept(s), for example but not by way of limitation, a 5 second reaction time may generate an oxygen concentration of 100 mm Hg, and a 10 second reaction time may generate an oxygen concentration of 50 mm Hg.

In a closed system, oxygen scavengers will bind oxygen present in an aqueous reagent and lower the oxygen level of the aqueous reagent. The oxygen level can vary, depending on the concentration of oxygen scavenger present, the reaction temperature, and the reaction time. In this manner, the defects and disadvantages of the prior art can be overcome, as different levels of oxygen can be generated by varying the oxygen scavenger concentration, the reaction temperature, and/or the reaction time, and the oxygen level so generated can be accurately measured using a by-product of the oxygen scavenger.

Compositions utilized in accordance with the presently disclosed and/or claimed inventive concept(s) include calibration and/or quality control reagent(s) and oxygen scavenger-containing reagent(s). When the calibration and/or quality control reagent is brought into contact with the oxygen scavenger, the oxygen scavenger removes oxygen from the aqueous reagent, thereby providing a desired oxygen level in the calibration and/or quality control reagent(s) based on the concentrations of oxygen scavenger(s) and/or calibration/quality control reagent(s) present in the reaction as well as the reaction time and/or the temperature at which the reaction occurs.

Any calibration and/or quality control reagent for use in the monitoring of the performance of various instrumentation(s) and for which a desired oxygen concentration must be maintained is encompassed within the scope of the presently disclosed and/or claimed inventive concept(s). In addition to the presence of oxygen, the calibration and/or quality control reagent(s) may further include any other component necessary for functionality thereof, including but not limited to, salt(s), protein(s), catalyst(s), analyte(s), metabolite(s), and/or gas(es). Such types of calibration and/or quality control reagents are well known in the art, and therefore no further discussion thereof is deemed necessary.

Any oxygen scavenger known in the art and capable of functioning as described or otherwise contemplated herein is encompassed within the scope of the presently disclosed and/or claimed inventive concept(s). That is, any reducing agent may function as an oxygen scavenger in accordance with the presently disclosed and/or claimed inventive concept(s) as long as the reducing agent is capable of (i) removing dissolved oxygen from a solution and (ii) capable of generating an electrochemically active by-product upon oxidation thereof that is chemically stable in aqueous solution. Examples of oxygen scavengers that may be utilized in accordance with the presently disclosed and/or claimed inventive concept(s) include, but are not limited to, a sulfite (such as, but not limited to, potassium sulfite or sodium sulfite), carbohydrazide, erythorbate, methylethylketoxime, hydroquinone, diethylhydroxylamine, as well as any combination thereof. However, other oxygen scavengers that are capable of functioning as described or otherwise contemplated herein are also well known in the art and encompassed by the presently disclosed and/or claimed inventive concept(s), and therefore no further discussion thereof is deemed necessary.

Any electrode known in the art and capable of functioning as described or otherwise contemplated herein is encompassed within the scope of the presently disclosed and/or claimed inventive concept(s). That is, any electrode may function as an electrode in accordance with the presently disclosed and/or claimed inventive concept(s) as long as the electrode is electrochemically active and is capable of being electrochemically reduced by the by-product of the oxygen scavenger so that an accurate concentration of oxygen present in the calibration and/or quality control reagent can be calculated out from the electrochemical current generated between the electrode and the scavenging by-products. A non-limiting example of an electrode that may be utilized in accordance with the presently disclosed and/or claimed inventive concept(s) includes a bare metal electrode. However, other electrodes that are capable of functioning as described or otherwise contemplated herein are also well known in the art and encompassed by the presently disclosed and/or claimed inventive concept(s), and therefore no further discussion thereof is deemed necessary.

Certain embodiments of the presently disclosed and/or claimed inventive concept(s) are directed to kits in which oxygen levels can be controlled (and/or specific oxygen levels can be generated) for calibration and/or quality control reagent(s); in addition, the generated desired oxygen levels can be accurately measured in the kits of these embodiments. These reagent(s) may be used for monitoring the performance of, for example but not by way of limitation, blood gas, electrolyte, and/or metabolite instrumentation. The kit includes at least one calibration and/or quality control reagent containing oxygen, as described herein above or otherwise contemplated herein. The kit further includes at least one second reagent that includes at least one oxygen scavenger. In certain embodiments, the oxygen scavenger-containing reagent may be in lyophilized or solidified form. When use of a calibration and/or quality control reagent is desired, a specific amount of the second reagent is combined with the calibration and/or quality control reagent so that the oxygen scavenger complexes with and reduces the amount of oxygen present in the calibration and/or quality control reagent. In this manner, a desired oxygen level can be provided in the calibration and/or quality control reagent(s) immediately before and/or at the time of use of such reagent(s).

The oxygen scavenger may be used at a molar ratio of less than or equal to 1:1 with the oxygen of the calibration and/or quality control reagent. A person of ordinary skill in the art would recognize that the resultant concentration of oxygen obtained in the calibration and/or quality control reagent(s) upon exposure to the oxygen scavenger is directly related to: (i) the initial concentration of oxygen in the calibration and/or quality control reagent; (ii) the concentration of oxygen scavenger present in the solid reagent, (iii) the amount of time that the oxygen scavenger-containing reagent is allowed to come into contact with the calibration and/or quality control reagent; and/or (iv) the temperature at which the reaction occurs. For example, but not by way of limitation, it may be desired to utilize a molar ratio of oxygen scavenger:oxygen in the calibration/quality control reagent of about 0.001:1, about 0.002:1, about 0.003:1, about 0.004:1, about 0.005:1, about 0.006:1, about 0.007:1, about 0.008:1, about 0.009:1, about 0.01:1, about 0.02:1, about 0.03:1, about 0.04:1, about 0.05:1, about 0.06:1, about 0.07:1, about 0.08:1, about 0.09:1, about 0.1:1, about 0.15:1, about 0.2:1, about 0.25:1, about 0.3:1, about 0.35:1, about 0.4:1, about 0.45:1, about 0.5:1, about 0.55:1, about 0.6:1, about 0.65:1, about 0.7:1, about 0.75:1, about 0.8:1, about 0.85:1, about 0.9:1, about 0.95:1, and about 1:1. Alternatively, it may be desired to utilize a molar ratio of oxygen scavenger:oxygen in the calibration/quality control reagent in a range of any of the above values (i.e., a range of from about 0.1:1 to about 1:1, or about 0.3:1 to about 0.9:1, etc.), and therefore any range formed from the combination of two values listed above is also encompassed within the scope of the presently disclosed and/or claimed inventive concept(s).

The reaction time may be any amount of time that allows for the oxygen scavenger-containing reagent to complex with oxygen in the calibration and/or quality control reagent and that is suitable for use with the methods and devices disclosed or otherwise contemplated herein. For example, but not by way of limitation, the reaction time may be about 0.001 second, about 0.002 second, about 0.003 second, about 0.004 second, about 0.005 second, about 0.006 second, about 0.007 second, about 0.008 second, about 0.009 second, about 0.01 second, about 0.05 second, about 0.1 second, about 0.15 second, about 0.2 second, about 0.25 second, about 0.3 second, about 0.35 second, about 0.4 second, about 0.45 second, about 0.5 second, about 0.55 second, about 0.6 second, about 0.65 second, about 0.7 second, about 0.75 second, about 0.8 second, about 0.85 second, about 0.9 second, about 0.95 second, about 1 second, about 2 seconds, about 3 seconds, about 4 seconds, about 5 seconds, about 6 seconds, about 7 seconds, about 8 seconds, about 9 seconds, about 10 seconds, about 11 seconds, about 12 seconds, about 13 seconds, about 14 seconds, about 15 seconds, about 16 seconds, about 17 seconds, about 18 seconds, about 19 seconds, about 20 seconds, about 25 seconds, about 30 seconds, about 35 seconds, about 40 seconds, about 45 seconds, about 50 seconds, about 55 seconds, about 60 seconds, about 65 seconds, about 70 seconds, about 75 seconds, about 80 seconds, about 85 seconds, about 90 seconds, about 95 seconds, about 100 seconds, about 105 seconds, about 110 seconds, about 115 seconds, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, and the like. Alternatively, it may be desired to utilize a reaction time within a range of any of the above values (i.e., a range of from about 0.01 second to about 20 minutes, or about 1 second to about 10 seconds, etc.), and therefore any range formed from the combination of two values listed above is also encompassed within the scope of the presently disclosed and/or claimed inventive concept(s).

Any reaction temperature known in the art may be utilized in accordance with the presently disclosed and/or claimed inventive concept(s) so long as the complexation of oxygen by the oxygen scavenger will occur at that temperature, and as long as the temperature is suitable for use with the methods and devices disclosed or otherwise contemplated herein. For example, but not by way of limitation, the reaction temperature may be about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., and the like. Alternatively, it may be desired to utilize a reaction temperature within a range of any of the above values (i.e., a range of from about 4° C. to about 37° C., or about 20° C. to about 26° C., etc.), and therefore any range formed from the combination of two values listed above is also encompassed within the scope of the presently disclosed and/or claimed inventive concept(s).

In certain embodiments, the calibration and/or quality control reagent(s) and/or oxygen scavenger-containing reagent(s) present in the kit may be aliquoted into single units thereof, or the kit may contain a volume of each reagent that constitutes multiple units thereof.

The calibration and/or quality control reagent(s) and/or oxygen scavenger-containing reagent(s) may be disposed in the kit in any form known in the art that allows the reagents to function in accordance with the presently disclosed and/or claimed inventive concept(s). For example, but not by way of limitation, the reagent(s) may be lyophilized and/or solidified. When the reagent(s) are lyophilized and/or solidified, the reagents(s) may be disposed in the kit in any form, including, but not limited to, a bead, a hemisphere, a cake, a tablet, or any other form, as well as any combination of these or other types of forms. In addition, when disposed in lyophilized and/or solidified form, the calibration and/or quality control reagent may also be maintained in a substantially air tight environment until use thereof.

When the oxygen scavenger-containing reagent(s) are disposed in lyophilized and/or solidified form, the kit may further include a diluent for reconstituting the reagent(s). The calibration and/or quality control reagent may function as a diluent for the solid reagent, or the diluent may be provided as a separate component of the kit. Any liquid reagent may be utilized as the diluent so long as the liquid reagent is compatible with both the oxygen scavenger-containing reagent(s) and the calibration and/or quality control reagent(s) and is capable of reconstituting the reagent(s). In one non-limiting example, the diluent is water, such as but not limited to, di-$H_2O$.

The kit may further include a sensor array that includes at least one electrode capable of electrochemically reducing the oxidation by-product of the oxygen scavenger. In certain non-limiting embodiments, the sensor array may further include a $pO_2$ sensor with which the calibration and/or quality control reagents are used.

Certain embodiments of the presently disclosed and/or claimed inventive concept(s) are also directed to methods of controlling an oxygen level (and/or generating a desired oxygen level) in a calibration and/or quality control reagent used in monitoring the performance of, for example, blood gas, electrolyte, and/or metabolite instrumentation. In the method, an oxygen level in any of the calibration and/or quality control reagents described in detail herein above or otherwise contemplated therein is controlled by exposure to a specific concentration of any of the oxygen scavenger-containing reagents described in detail herein above or otherwise contemplated herein, wherein the oxygen scavenger-containing reagent complexes with a specific amount of oxygen and thereby provides a desired level of oxygen in the calibration and/or quality control reagent at the time of use. The calibration and/or quality control reagent containing the desired oxygen level is then used to monitor the performance of blood gas, electrolyte, and/or metabolite instrumentation, and the reagent contains a desired oxygen level based upon the concentration of the oxygen scavenger and the reaction time and reaction temperature of the exposure.

A person of ordinary skill in the art would recognize that the amount of oxygen complexed by the oxygen scavenger is directly related to the amount of oxygen scavenger that is allowed to come into contact with the calibration and/or quality control reagent as well as the time and temperature at which the reaction occurs. The exposure is performed at a specific reaction temperature and for a specific amount of time (as described in detail herein above and/or otherwise contemplated herein) and may occur immediately prior to the use of the calibration and/or quality control reagent.

Certain embodiments of the method also include accurately measuring the oxygen level so generated. In these embodiments, a concentration of a by-product of the oxygen scavenger produced upon oxidation thereof is measured, whereby the concentration of the by-product is in direct proportion to the amount of oxygen consumed by the oxygen scavenger. An accurate concentration of oxygen present in the calibration and/or quality control reagent can then be calculated by subtracting the concentration of the by-product from the original oxygen concentration present in the calibration and/or quality control reagent.

The presently disclosed and/or claimed inventive concept(s) is additionally directed to a device capable of controlling an oxygen level (and/or generating different oxygen levels) in a calibration and/or quality control reagent for monitoring the performance of, for example, blood gas, electrolyte, and/or metabolite instrumentation; the device may also be capable of accurately measuring the oxygen level so generated. In certain non-limiting embodiments, the device is a sensor cartridge, such as but not limited to, a single-use sensor cartridge. The device includes any of the calibration and/or quality control reagents comprising oxygen described in detail herein above, as well as any of the oxygen scavenger-containing reagents as described in detail herein above. In one embodiment, the device contains at least two cavities. A predetermined amount of the calibration and/or quality control reagent is disposed in a first cavity, while a predetermined amount of the oxygen scavenger-containing reagent is disposed in a second cavity. The first cavity is defined as an activatable cavity, and said cavity is capable, upon activation thereof, of being in fluidic communication with the second cavity. Upon activation of the activatable cavity, the calibration and/or quality control reagent moves from the activatable cavity into the second cavity, whereby the oxygen scavenger-containing reagent reduces the amount of oxygen present in the calibration and/or quality control reagent, thereby providing a desired oxygen level in the calibration and/or quality control reagent. As described in detail herein above, a person of ordinary skill in the art would recognize that the amount of oxygen removed from the calibration and/or quality control reagent is directly related to the amount of oxygen scavenger that is allowed to come into contact with the calibration and/or quality control reagent as well as the time and temperature at which the reaction occurs.

The device may further include a sensor array, wherein the sensor array includes a sensor (such as, but not limited to, a $pO_2$ sensor) and an electrode. Once the desired oxygen level is generated, the oxygen level so generated can be accurately measured using the electrode; the electrochemically active by-product of the oxidation of the oxygen scavenger is reduced upon contact with the electrode, and the concentration of the by-product is directly proportional to the concentration of oxygen removed from the original calibration and/or quality control reagent. Next, the calibration and/or quality control reagent can be brought into contact with the sensor, such as but not limited to a $pO_2$ sensor, thus allowing for calibration of the sensor.

The sensor array may be present in the second cavity; alternatively, the device may comprise a third cavity that is capable of being in fluidic communication with the second cavity, and this third cavity contains the sensor array. In yet another, non-limiting embodiment, the sensor and electrode of the sensor array may be disposed in different cavities; in this embodiment, one of the sensor and the electrode may be disposed in the second cavity and the other disposed in a third cavity, or the sensor and the electrode may be disposed in third and fourth cavities.

In one particular, non-limiting embodiment, the oxygen scavenger-containing reagent may be disposed in the second cavity in lyophilized or solidified form. In this embodiment, the calibration and/or quality control reagent may act as a diluent for reconstitution of the lyophilized and/or solidified oxygen scavenger-containing reagent.

As stated herein above, the instrumentation may further include a sensor. The sensor may be any sensor useful with, for example, blood gas, electrolyte, and/or metabolite instrumentation. Said sensors are well known in the art, and therefore no further discussion thereof is deemed necessary.

In construction of the device, at least a portion of the device may be sealed to maintain the calibration and/or quality control reagent in a substantially airtight environment until use thereof; this prevents exposure of the calibration and/or quality control reagent to humidity that could interfere with the composition or physical structure of the calibration and/or quality control reagent. The calibration and/or quality control reagent may be disposed in the first cavity (as described herein above) by any method known in the art.

The activatable cavity may be activated by any method known in the art or otherwise contemplated herein; for example, but not by way of limitation, the activatable cavity may be in the form of a blister pack and/or barrier pouch, and the disposal of pressure thereon results in depression thereof, followed by flow of the calibration and/or quality control reagent and thus the combination of said reagent with the oxygen scavenger-containing reagent (as described herein above).

In certain embodiments, the device may further include a plurality of cavities, each having disposed therein a predetermined amount of any of the calibration and/or quality control reagents and/or any of the oxygen scavenger-containing reagents described in detail herein above or otherwise contemplated herein. In addition, the plurality of cavities may contain other reagents related to the use of the device.

Non-limiting examples of devices constructed with the arrangement described herein (i.e., a cavity containing a lyophilized reagent and an activatable cavity containing a reagent that may act as a diluent therefor) are described in detail in published International Application No. WO2013/078130, published May 30, 2013, the entire contents thereof are expressly incorporated herein by reference. The devices of the presently disclosed and/or claimed inventive concept(s) will be understood to be capable of possessing the same structural features as disclosed in said reference, as well as to be capable of production and use in an identical manner as the devices disclosed therein. Thus, no further description (in the form of descriptive language and/or drawings) of the structure, production, and/or use of the device of the presently disclosed and/or claimed inventive concept(s) is deemed necessary.

The presently disclosed and/or claimed inventive concept(s) is also directed to a method for monitoring the performance of blood gas, electrolyte, and/or metabolite instrumentation. In the method, any of the devices described herein above or otherwise contemplated herein is disposed into a blood gas, electrolyte, and/or metabolite instrumentation, and the device is activated at a certain temperature and for a certain period of time to provide a desired oxygen level for the calibration and/or quality control reagent. The reagent containing the desired oxygen level is then brought into contact with a $pO_2$ sensor for calibration and/or quality control of the blood gas, electrolyte, and/or metabolite instrument.

Any of the "disposing" and/or "activating" steps described herein may be performed, for example but not by way of limitation, by a user. However, as used herein, the term "user" is not limited to use by a human being; rather, the term "user" may comprise (for example, but not by way of limitation) a computer, a server, a website, a processor, a network interface, a human, a user terminal, a virtual computer, combinations thereof, and the like.

In certain embodiments of the method, the oxygen level generated in the calibration and/or quality control reagent upon activation of the device is accurately measured. In these embodiments, a concentration of the by-product of the oxygen scavenger produced upon oxidation thereof is measured, whereby the concentration of the by-product is in direct proportion to the amount of oxygen consumed by the oxygen scavenger. The concentration of the by-product is measured by contacting the calibration and/or quality control reagent with the electrode present in the device; the electrochemically active by-product of the oxidation of the oxygen scavenger is reduced upon contact with the electrode, and the concentration of the by-product is directly proportional to the concentration of oxygen removed from the original calibration and/or quality control reagent. An accurate concentration of oxygen present in the calibration and/or quality control reagent that is brought into contact with the sensor can then be calculated by subtracting the concentration of the by-product from the original oxygen concentration present in the calibration and/or quality control reagent.

The various embodiments of compositions, kits, devices, and methods of the presently disclosed and/or claimed inventive concept(s) may be utilized with any blood gas, electrolyte, and/or metabolite instrument for which calibration and/or quality control is desired. In certain, non-limiting embodiments, the instrument may be a point of care instrument. The blood gas, electrolyte, and/or metabolite instrument may be a system or systems that are able to embody and/or execute the logic of the methods/processes described herein. Logic embodied in the form of software instructions and/or firmware may be executed on any appropriate hardware. For example, logic embodied in the form of software instructions and/or firmware may be executed by one or more components on a dedicated system or systems, on a personal computer system, on a distributed processing computer system, and/or the like. In some embodiments, the entire logic may be implemented in a stand-alone environment operating on an instrument (such as, but not limited to, a point of care instrument). In other embodiments, the logic may be implemented in a networked environment such as a distributed system in which multiple instruments collect data that is transmitted to a centralized computer system for analyzing the data and supplying the results of the analysis to the instruments. Each element of the instrument may be partially or completely network-based or cloud based, and may or may not be located in a single physical location.

Circuitry used herein includes (but is not limited to) analog and/or digital components, or one or more suitably programmed processors (e.g., microprocessors) and associated hardware and software, or hardwired logic. Also, "components" may perform one or more functions. The term "component" may include hardware, such as but not limited to, a processor (e.g., microprocessor), an application specific integrated circuit (ASIC), field programmable gate array (FPGA), a combination of hardware and software, and/or the like.

Software utilized herein may include one or more computer readable medium (i.e., computer readable instructions) that when executed by one or more components cause the component to perform a specified function. It should be understood that the algorithms described herein may be stored on one or more non-transient memory. Non-limiting exemplary non-transient memory may include random access memory, read only memory, flash memory, and/or the like. Such non-transient memory may be electrically based, optically based, and/or the like.

Thus, in accordance with the presently disclosed and/or claimed inventive concept(s), there have been provided compositions, kits, and devices, as well as methods of producing and using same, which fully satisfy the objectives and advantages set forth hereinabove. Although the inventive concept(s) has been described in conjunction with the specific language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed and/or claimed inventive concept(s).

What is claimed is:

1. A kit for generating different specific oxygen levels in an aqueous calibration and/or quality control solution used in monitoring the performance of blood gas, electrolyte, and/or metabolite instrumentation, the kit comprising:
   (a) at least one aqueous calibration and/or quality control solution comprising oxygen and used in monitoring the performance of blood gas, electrolyte, and/or metabolite instrumentation, wherein a specific oxygen level must be maintained in the calibration and/or quality control solution when monitoring the performance of the instrumentation;
   (b) a reagent comprising at least one oxygen scavenger for generating one or more specific oxygen levels in (a), wherein the reagent comprising the at least one oxygen scavenger is disposed in the kit as a separate component from (a) and is not combined with (a) while present in the kit; and
   wherein, when use of the at least one aqueous calibration and/or quality control solution is desired, a specific amount of (b) is combined with (a) so that the oxygen scavenger in (b) complexes oxygen present in (a), thereby providing a desired oxygen level in the at least one aqueous calibration and/or quality control reagent solution, wherein the desired oxygen level so generated is in a range of from about 50 mm Hg to about 150 mm Hg.

2. The kit of claim 1, wherein (b) is lyophilized or solidified.

3. The kit of claim 1, wherein each of (a) and (b) is separately disposed in a substantially air tight environment until use thereof.

4. The kit of claim 1, wherein the oxygen scavenger is selected from the group consisting of a sulfite, carbohydrazide, erythorbate, methylethylketoxime, hydroquinone, diethylhydroxylamine, and combinations thereof.

5. The kit of claim 1, wherein the oxygen scavenger of (b) is present at a molar ratio of less than or equal to about 0.5:1 with the oxygen of (a).

6. The kit of claim 1, further comprising:
   (c) a sensor array comprising at least one electrode capable of electrochemically reducing an oxidation by-product of the oxygen scavenger of (b); and
   wherein the by-product is measured using the electrode of (c) to calculate an accurate oxygen level in the at least one aqueous calibration and/or quality control solution.

7. The kit of any claim 6, wherein the electrode of (c) is a bare metal electrode.

8. The kit of claim 6, wherein (c) further comprises a $pO_2$ sensor with which (a) is used for calibration thereof.

* * * * *